United States Patent [19]
Viljava et al.

[11] Patent Number: 5,932,455
[45] Date of Patent: Aug. 3, 1999

[54] METHOD FOR PREPARING PURE LACTIC ACID

[75] Inventors: Tapio Viljava; Hannu Koivikko, both of Kantvik, Finland

[73] Assignee: Cultor Oy, Helsinki, Finland

[21] Appl. No.: 08/945,874

[22] PCT Filed: Jul. 16, 1996

[86] PCT No.: PCT/FI96/00415

§ 371 Date: Nov. 7, 1997

§ 102(e) Date: Nov. 7, 1997

[87] PCT Pub. No.: WO97/04120

PCT Pub. Date: Feb. 6, 1997

[30] Foreign Application Priority Data

Jul. 18, 1995 [FI] Finland ................................ 953480

[51] Int. Cl.⁶ ....................................................... C12P 7/56
[52] U.S. Cl. ......................... 435/139; 435/822; 435/853; 435/885
[58] Field of Search ................................ 435/139, 822, 435/853, 885

[56] References Cited

U.S. PATENT DOCUMENTS

| | | | |
|---|---|---|---|
| 4,156,630 | 5/1979 | Muller | 435/261 |
| 4,355,117 | 10/1982 | Antrim et al. | 435/179 |
| 4,771,001 | 9/1988 | Bailey et al. | 435/139 |
| 4,865,969 | 9/1989 | Amen et al. | 435/802 |
| 4,882,277 | 11/1989 | Czytko et al. | 435/139 |
| 5,464,760 | 11/1995 | Tsai et al. | 435/139 |
| 5,503,750 | 4/1996 | Russo et al. | 210/641 |
| 5,635,368 | 6/1997 | Lommi et al. | 435/139 |

FOREIGN PATENT DOCUMENTS

| | | |
|---|---|---|
| 0 487 867 A1 | 6/1992 | European Pat. Off. . |
| 913344 | 12/1992 | Finland . |
| 3715857 A1 | 12/1988 | Germany . |

OTHER PUBLICATIONS

Gerhartz, W., et al., "Ethanolamines to Fibers," Ullman's Encyclopedia of Industrial Chemistry, 5th Ed., vol. A10, VCH Publishers, Inc. New York, pp. 157–158, 1987.

*Primary Examiner*—Herbert J. Lilling
*Attorney, Agent, or Firm*—Sterne, Kessler, Goldstein & Fox P.L.L.C.

[57] ABSTRACT

The invention relates to a method for preparing pure lactic acid or a salt thereof by fermentation. The preparation process comprises bioreactor refreshing cycle and a lactic acid production cycle, wherein during the production cycle a solution comprising substantially pure feedstock is recycled through a bioreactor containing refreshed microorganism cells, the lactic acid produced being neutralized by adding an alkali, and the recycling is discontinued when the alkali consumption is substantially diminished, and during the refreshing cycle the microorganism cells are refreshed by recycling through the bioreactor a carbohydrate solution enriched with nutrients, thus replenishing the capacity of the microorganisms to produce an acid, and recovery of lactate or conversion thereof into lactic acid or other salt.

17 Claims, No Drawings

METHOD FOR PREPARING PURE LACTIC ACID

The present invention relates to a novel method for preparing pure lactic acid or a salt thereof by fermentation.

During the production cycle a solution comprising substantially pure feedstock is recycled through a bioreactor containing refreshed microorganism cells, such as bacterial cells or fungal mycelium.

During the refreshing cycle the microorganism cells are refreshed by recycling a feedstock solution enriched with nutrients, thus replenishing the capacity of the microorganisms to produce lactic acid.

FIELD OF THE INVENTION

Lactic acid is produced both by fermentation and by synthetic methods for a wide variety of applications. The purity of the product grades varies from technical lactic acid to slightly more purified food grade, and further to pharmaceutical grade. Often when lactic acid is employed as feedstock in an organic synthesis, a product of exceptionally pure thermally stable grade is necessary. Inexpensive lactic acid prepared by fermentation has generally been used for technical and food applications. Pharmaceutical and exceptionally pure (thermally stable) grades of lactic acid, on the other hand, have normally been produced by synthetic processes by which a comparatively pure product is directly obtained. Proper purification of lactic acid prepared by fermentation is known to be a cumbersome process requiring many steps, thus making up a large part of the production costs.

A new, ever increasing application for exceptionally pure (thermally stable) lactic acid is the preparation of lactide polymers. Lactide is a cyclic ester formed by two lactic acid molecules that can be controlledly polymerized. Polylactide is biologically degradable, on account of which property it is employed as a material for producing controlledly biodegradable support and attachment members used in bone surgery. Furthermore, on account of this property polylactide is considered as a potential raw material for compostable plastics. In addition to thermal stability, high optical purity is required of lactic acid employed to produce polylactides. Synthetically produced lactic acid is an equimolar mixture of the two optical isomers, and high-grade plastic cannot be prepared therefrom. On the other hand, nearly pure optical isomers can be produced by fermentation, by selecting a suitable producer organism. There are several possible homofermentative lactic acid bacteria for example of the genera Lactobacillus, Streptococcus and Pediococcus, such as *Lactobacillus delbrückii* for the preparation of L-lactic acid and *Lactobacillus bulgaricus* for the preparation of D-lactic acid.

The preparation of lactic acid by fermentation normally takes place by fermenting one batch at a time. It is also known to prepare lactic acid continuously with bacteria bound to a solid carrier and also by normal mixed fermentation. In all these methods, the production of lactic acid is strongly dependent on the growth of the bacterial population. Lactic acid bacteria are known to require a rich medium for growth, as their capacity to synthesize the growth factors they need is very small. Hence B group vitamins and a wide variety of different amino acids must be added to the medium. This addition is often made from yeast extract, which is typically needed in an amount of at least one tenth of the amount of sugar feedstock. The cost for such an amount of yeast extract is of the same order as that of sugar. That part of the nutrients which is not bound to the growing biomass remains in the product, thus lowering its purity. A special problem is presented by the nitrogenous nutrient components in view of preparing a thermally stable grade.

In light of the foregoing, it can be concluded that an ideal fermentation process for the industrial preparation of pure lactic acid would be a process that produced an essentially purer product than the hitherto known processes, necessitated substantially less nutrients than the hitherto known methods, and produced essentially less biomass. The invention to be described below meets these requirements.

DESCRIPTION OF THE INVENTION

It has now been found that in the preparation of lactic acid, the actual fermentation reaction and the culturing of producer organisms can be separated into discrete production and refreshing cycles. In the culturing stage, i.e. refreshing cycle, the rich nutrient medium is passed through the bioreactor for a few hours. After the culturing stage, pure feedstock solution that reacts into lactic acid can be passed through the bioreactor. A carbohydrate, e.g. starch or other polysaccharide, such as polydextrose or inulin, or sucrose, lactose or glucose, or other mono-, di- or oligosaccharides or a mixture of these may be used as feedstock.

Suitable producer organisms include natural and/or selected microorganisms or microorganisms produced by adaptation or mutated to produce a desired lactic acid. Preferred producer organisms include first of all lactic acid bacteria, such as those of the genera Aerococcus, Carbobacterium, Enterococcus, Erysipelothrix, Gemella, Globicatella, Lactobacillus, Lactococcus, Leuconostoc, Pediococcus, Streptococcus, Tetragenococcus and Vagococcus. Also moulds, such as Rhizopus, may be employed. Particularly preferred microorganisms include *Lactococcus Lactis, Lactobacillus delbrückii, Lactobacillus bulgaricus* and *Lactobacillus leichmanii*, and *Rhizopus oryzae*.

The producer organism is retained in the bioreactor equipment. Preferably the producer organism is bound to a solid carrier. Retention of the microorganism in the bioreactor can also be achieved by microfiltration membrane technique, for example.

The bioreactor equipment comprises for example a stirred tank reactor, multi-duct tube reactor, basket reactor, fluidized bed reactor, packed bed reactor or filter reactor.

A packed bed reactor is preferably used.

The carrier is preferably substantially incompressible and preferably comprises a continuous matrix having a large surface area or, alternatively, porous or reticular grains having a large surface area. The matrix or grains again comprise discrete microparticles or microfibres. Such a carrier material texture affords maximum surface area in view of the immobilization of the bacterial cells. The carrier typically has a binding capacity of $10^8$–$10^{13}$ cells/1 ml of carrier.

In accordance with a particularly preferred embodiment, the carrier material comprises microfibres or microparticles of diethylaminoethyl-substituted cellulose (DEAE cellulose) adhesively bonded with agglomeration to polystyrene (cf. U.S. Pat. No. 4,355,117). Other suitable agglomerizing substances include melamine formaldehyde resin and epoxy resins, for instance (cf. DE 31 30 178 C2).

Porous, sintered glass or a ceramic material may also be employed as the carrier.

The producer organism is bound to a solid carrier that is packed into a bioreactor. In the refreshing cycle, a feedstock solution enriched with nutrients, such as yeast extract and other nutrients, is recycled through the reactor. A carbohydrate may be employed as feedstock, as stated above. Recycling of nutrients will produce growth in the microorganism, and hence an acid is produced in principle in the same way as in conventional preparation of lactic acid by fermentation. To prevent end product inhibition, the pH of the solution is maintained constant, generally at 5–8.5, preferably at 5.5–8.0, by adding an alkali, e.g. a sodium hydroxide solution, as lactic acid is produced. The refreshing is observed by monitoring the consumption of alkali, and after this consumption has taken a steep turn upward the refreshing is discontinued, the refreshing solution is displaced from the bioreactor by water and the production cycle is started. The temperature in the refreshing solution tank is maintained so high (generally in excess of 60–80° C.) or so low (generally below 4° C.) that the growth of the microorganism in the tank is inhibited. The same refreshing solution is used several times over. A depleted refreshing solution is conventional lactate produced by fermentation.

The production cycle employs a pure feedstock solution that is recycled through the refreshed bioreactor. The temperature is maintained at optimum in view of the operation of the microorganism, in other words, generally at 5–65° C., even as high as 80–85° C. The optimum temperature for many microorganisms is 15–60° C. To prevent end product inhibition, the pH of the recycled solution is maintained constant, normally at 5–7, preferably at 5.5–6.5, by adding an alkali as lactic acid is produced. The new detached cells that are initially entrained in the recycling are again bound to the carrier during the production cycle, and thus the recycled solution will remain clear. After the refreshing, the acid production capacity will remain adequate for several days. When the feedstock is depleted, the result is, on visual estimate, a clear and pure lactate solution that can be converted into lactic acid by normal cation exchange. The product solution is displaced from the bioreactor by water, and superfluous bacteria are removed by backwash prior to the next refreshing cycle.

A refreshing cycle is started when the production capacity of the microorganism is essentially diminished. The microorganism is refreshed at intervals of 0.5–30 days.

The lactate solution obtained is supplied to the cation exchange via slight check-up filtering; no separate cell mass separation step is needed. In addition to converting lactate into acid, the cation exchange removes dissolved metals and other foreign cations from the product.

The ion-exchanged lactic acid solution is concentrated by evaporation. In addition to water, acetic acid, butyric acid and other volatile acids constituting a large part of the impurities produced in the fermentation are then removed from the product.

Actual separation and recovery methods are therefore not needed, since the lactic acid solution already at this stage has higher purity than lactic acid produced by conventional methods subsequent to several purification steps. The light colour developed in the solution can be removed by conventional adsorption methods known in industry for example by activated carbon and/or adsorbent resins. The advantages of the invention over the prior art are the following:

1. Nutrients, such as yeast extract, are only consumed in an amount that is a fraction of the conventional amount.

2. The production of biomass has been minimized, and the majority of the bacteria or mycelium are passed over for utilization in the next batch.

3. The product is nearly free of nutrient components and microorganism cells, and thus the post-purification is simple and inexpensive.

In regard to purity, the advantage derived from the invention is naturally dependent on the purity of the feedstock employed.

The examples to be set forth below illustrate the invention more closely, yet without restricting the applicability of the invention for example with regard to selection of the microorganism or reactor, the immobilization method, or other details. What is essential is the efficient separation of the culturing and production cycles. In the examples, all per cent values are indicated as weight per cent.

EXAMPLE 1

Pretreatment of Carrier, Loading of Bioreactor and Binding of Cells

Granular DEAE cellulose, Spezymer GDC 220, having a grain size of 350–850 $\mu$m and prepared in accordance with U.S. Pat. No. 4,355,117, was used as a carrier for the cells. Carrier pretreatment, packing of the bioreactor and binding of the bacterial cells were carried out as follows:

600 g of granular DEAE cellulose was reduced to a slurry in water and soaked for five hours with occasional stirring. The hydrated carrier was poured into a glass column serving as a bioreactor and having an inner diameter of 50 mm and a height of 100 cm. The height of the carried bed formed was about 75 cm. The remainder of the bioreactor volume was filled with water.

The carrier bed was sterilized by displacing the water with a 2% sodium hydroxide solution and recycling it through the bioreactor for 2 hours at a temperature of 60° C. After sterilization, the hot lye was displaced with water, and the bed was neutralized by pumping a 2% sulphuric acid through the bed until the pH of the outflow was below 6.0. As a last step, the bed was flushed with water.

*Lactobacillus delbrückii* bacteria were cultured for 16 hours at a temperature of 40° C. on an MRS culture medium (de Man, J. C., Rogosa, M., Sharpe, M. E., *J. Appl. Bacteriol.* 23, 130–135, 1960). 300 ml of a bacterial culture thus obtained, containing about $10^9$ bacteria/ml of solution, was slowly pumped through the bioreactor; the majority of the bacteria being bound to the carrier.

EXAMPLE 2

First Refreshing of Cells

A culture medium was produced in a refreshing solution tank having a volume of 3 liters and being provided with a mixer, by dissolving in water 100 g of solid glucose, 8 g of yeast extract, 0.2 g of magnesium sulphate ($MgSO_4$) and 0.2 g of manganous sulphate ($MnSO_4$) to give a total solution volume of 2 liters. The solution and tank were sterilized by autoclaving at a temperature of 121° C.

The culture medium thus produced was pumped into the bioreactor from the bottom so that it displaced the water that was present in the bioreactor, which was withdrawn from the upper end of the bioreactor. When the water outflow from the bioreactor started changing into culture medium, the pumping direction was reversed so that the culture medium was conveyed into the bioreactor from the top and the outflow solution from the bioreactor was conveyed back to the refreshing tank. The culture medium was thus recycled from the refreshing solution tank to the bioreactor and back at a volumetric flow rate of 15 l/h with a refreshing solution tank temperature of 60° C. and bioreactor temperature of 40° C.

The passage of the refreshing solution was observed by measuring the pH of the refreshing tank. The lactic acid produced in connection with the refreshing was neutralized by adding a 10-molar sodium hydroxide solution to the refreshing tank so that the pH of the content of the tank remained at 6.5. Four hours from the start of the refreshing, the sodium hydroxide consumption took a steep turn upwards as an indication of the fact that the bacteria had started growing exponentially, and the refreshing was discontinued. The culture medium present in the bioreactor was displaced by pumping water through the bottom simultaneously as the outflow solution from the bioreactor was reintroduced into the refreshing solution tank. When the outflow solution from the bioreactor became colourless, the pumping was discontinued.

EXAMPLE 3

Production of Lactate

A pure glucose solution was prepared in a tank having a capacity of 3 liters, by dissolving 120 g of crystalline glucose in water to give a total solution volume of 2 liters. The glucose solution and tank were sterilized by autoclaving at a temperature of 121° C.

The glucose solution produced was pumped into the bioreactor from below so that it displaced the water present in the bioreactor which was conveyed to drain. When the water outflow from the bioreactor started changing into glucose solution, the pumping direction was reversed in such a way that the glucose solution was conveyed to the bioreactor from the top and the solution outflow from the bioreactor was conveyed back to the tank. The glucose solution was thus recycled from the tank to the bioreactor and back at a volumetric flow rate of 15 l/h with a tank and bioreactor temperature of 40° C. The progress of the bioreaction was observed by measuring the pH of the content of the tank. The lactic acid produced was neutralized by adding a 10-molar sodium hydroxide solution to the tank so that the pH of the content of the tank remained at 6.5. Three days from the start of the production cycle the consumption of sodium hydroxide had ended and the recycling was discontinued. The sodium lactate solution present in the bioreactor was displaced by pumping water through the bottom simultaneously as the outflow solution from the bioreactor was conveyed back to the tank. When the sodium lactate solution outflow from the bioreactor started turning into water, pumping was discontinued.

EXAMPLE 4

Ion Exchange of Lactate into Lactic Acid

The sodium lactate solution prepared in Example 3 was conveyed at a volumetric flow rate of 1000 ml/h to a glass column having an inner diameter of 50 mm and containing 1000 ml of a cation exchange resin Relite C 360, manufacturer Mitsubishi Chemical Industries. A clear, yellowish lactic acid solution was obtained as a product.

The ash content of the product was analyzed by burning, the nitrogen content by the Antek method, the total lactic acid content by liquid chromatography with ion exchange resin in hydrogen form and the L-lactic acid content by the Boehringer-Ingelheim enzymatic method. The total purity thus obtained was 97% of lactic acid on dry solids; 95% of the lactic acid was L-lactic acid. The ash content was 0.1% on dry solids and the nitrogen content 0.08% on dry solids.

The ion exchange column was regenerated for the next cycle by conveying 1400 ml of 5% hydrochloric acid therethrough, flushing with 2000 ml of water and finally backwashing with 3000 ml of water.

EXAMPLE 4a

Ion Exchange of Lactate into Lactic Acid

The experiment of Example 4 was repeated using *Lactococcus lactis* bacteria as microbes.

The sodium lactate solution prepared in Example 3 was conveyed at a volumetric flow rate of 1000 ml/h to a glass column having an inner diameter of 50 mm and containing 1000 ml of a cation exchange resin Relite C 360, manufacturer Mitsubishi Chemical Industries. A clear, yellowish lactic acid solution was obtained as a product.

The ash content of the product was analyzed by burning, the nitrogen content by the Antek method, the total lactic acid content by liquid chromatography with ion exchange resin in hydrogen form and the L-lactic acid content by the Boehringer-Ingelheim enzymatic method. The total purity thus obtained was 97% of lactic acid on dry solids; 98% of the lactic acid was L-lactic acid. The ash content was 0.07% on dry solids and the nitrogen content 0.01% on dry solids.

The ion exchange column was regenerated for the next cycle by conveying 1400 ml of 5% hydrochloric acid therethrough, flushing with 2000 ml of water and finally backwashing with 3000 ml of water.

EXAMPLE 5

Second Refreshing and Production

The bioreactor produced in Example 1, wherefrom the sodium lactate product had been displaced in the manner described in Example 3, was prepared for the next refreshing and production cycles by backwash with water. At the onset of washing, a turbid bacterial suspension came off the bed and was conveyed to drain. Thereafter the flow direction of washing water was reversed from top to bottom and the washing was continued until the effluent water was clear.

The culture medium partly reacted into lactic acid, which had remained in the refreshing solution tank in Example 2, was used as such for the next refreshing. The water present in the bioreactor was displaced by pumping refreshing solution into the reactor from the bottom. When the water outflow from the bioreactor started changing into culture medium, the pumping direction was reversed so that the solution outflow from the bioreactor was conveyed back to the refreshing solution tank. The second refreshing was performed in the manner described in Example 2 and was discontinued after four hours, whereafter a new lactate production cycle was performed in the manner described in Example 3.

A total of 10 successive refreshing and production cycles were performed, employing in the refreshing cycle the same culture medium that was prepared in Example 2, whereafter the refreshing solution tank was emptied and a new culture medium was produced.

We claim:

1. A method for producing lactic acid or a salt thereof by fermentation, said method comprising:

(1) fermenting bacterial cells or fungal mycelium in a fermentation process that comprises (A) a refreshing cycle during which a solution that comprises a feedstock solution enriched with nutrient medium is recycled through a bioreactor that contains bacterial cells or fungal mycelium that have previously been fermented, wherein said refreshing cycle is sufficient to replenish the capacity of said cells or said mycelium to produce said lactic acid; and (B) a production cycle during which a solution which comprises a substantially pure carbohydrate feedstock is recycled through said bioreactor, wherein said bioreactor contains the bacterial cells or fungal mycelium that have been refreshed as in part (A), wherein said refreshing cycle and said production cycle are separate cycles; and (2) producing said lactic acid during said production cycle.

2. A method as claimed in claim 1, wherein the carbohydrate is selected from the group consisting of starch, polydextrose, inulin, sucrose, lactose, glucose, other mono-, di- or oligosaccharides or a mixture of these.

3. A method as claimed in claim 2, wherein the bioreactor equipment comprises a stirred tank reactor, multi-duct tube reactor, basket reactor, fluidized bed reactor, packed bed reactor or filter reactor.

4. A method as claimed in claim 3, wherein microorganism cells bound to a carrier are employed.

5. A method as claimed in claim 4, wherein the carrier has a binding capacity of $10^8$–$10^{13}$ cells/1 ml of carrier.

6. A method as claimed in claim 1, wherein the refreshing cycle is started when the production capacity of the microorganism is essentially diminished.

7. A method as claimed in claim 1, wherein the microorganism is refreshed at intervals of 0.5–30 days.

8. A method as claimed in claim 1, wherein a refreshing solution employed for refreshing is maintained in a refreshing tank at a temperature greater than 60–80° C., or at a temperature below 4° C. to inhibit the growth of the microorganism.

9. A method as claimed in claim 1, wherein the pH of the solution recycled through the bioreactor is maintained at 5–8.5, or at 5.5–8.0.

10. A method as claimed in claim 1, wherein the temperature of the bioreactor is optimal for the operation of the microorganism.

11. A method as claimed in claim 4, wherein the carrier is substantially non-compressible and preferably comprises a continuous matrix having a large surface area or, alternatively, porous or reticular grains having a large surface area.

12. A method as claimed in claim 1, wherein the microorganism is selected from lactic acid-producing bacterium and fungal mycelium.

13. A method as claimed in claim 12, wherein the microorganism is selected from the genera Lactococcus, Lactobacillus, Streptococcus, Pediococcus, or from Rhizopus.

14. A method as claimed in claim 1, wherein during the production cycle substantially the entire carbohydrate content is converted into lactate, at which point the recycling is discontinued as the alkali consumption has substantially ended.

15. A method as claimed in claim 13, wherein the microorganism selected for the preparation of L-lactic acid is *Lactococcus lactis* or *Lactobacillus delbruckii*.

16. A method as claimed in claim 13, wherein the Lactobacillus selected for the preparation of D-lactic acid is *Lactobacillus bulgaricus*.

17. A method as claimed in claim 13, wherein the Rhizopus is *Rhizopus oryzae*.

* * * * *